US009731975B2

(12) United States Patent
Katsoulis et al.

(10) Patent No.: US 9,731,975 B2
(45) Date of Patent: Aug. 15, 2017

(54) ALTERNATIVE METHODS FOR THE SYNTHESIS OF ORGANOSILICON COMPOUNDS

(75) Inventors: Dimitris E Katsoulis, Midland, MI (US); Malcolm E Kenney, Cleveland Heights, OH (US); Plousia E Vassilaras, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 415 days.

(21) Appl. No.: 14/384,540

(22) PCT Filed: Mar. 16, 2012

(86) PCT No.: PCT/US2012/029402
§ 371 (c)(1),
(2), (4) Date: Sep. 11, 2014

(87) PCT Pub. No.: WO2013/137904
PCT Pub. Date: Sep. 19, 2013

(65) Prior Publication Data
US 2015/0023861 A1     Jan. 22, 2015

(30) Foreign Application Priority Data
Mar. 15, 2012   (EP) .................................... 12159739

(51) Int. Cl.
*C01B 33/08*     (2006.01)
*C07F 7/12*     (2006.01)
*C07C 17/26*     (2006.01)

(52) U.S. Cl.
CPC .............. *C01B 33/08* (2013.01); *C07C 17/26* (2013.01); *C07F 7/123* (2013.01)

(58) Field of Classification Search
CPC .......... C01B 33/08; C07C 7/123; C07C 17/26
See application file for complete search history.

(56) References Cited

U.S. PATENT DOCUMENTS

| 4,448,981 | A | * | 5/1984 | Tolentino | .............. | C07C 17/093 |
| | | | | | | 556/459 |
| 4,855,473 | A | * | 8/1989 | Wurminghausen | ..... | C07F 7/188 |
| | | | | | | 556/471 |

(Continued)

OTHER PUBLICATIONS

International Search Report of PCT/US2012/029402 mailed Feb. 5, 2014.

(Continued)

*Primary Examiner* — Colleen Dunn
(74) *Attorney, Agent, or Firm* — Brinks Gilson & Lione

(57) ABSTRACT

A method of forming chloro-substituted silanes from the reaction of an alkoxysilane with a chlorinating agent in the optional presence of a catalyst is provided. More specifically, chloro-substituted silanes, including but not limited to silicon tetrachloride, are formed by reacting a chlorinating agent, such as thionyl chloride, with an alkylalkoxysilane having the formula $(R'O)_{4-x}SiR_x$, where R and R' are independently selected alkyl groups comprising one or more carbon atoms and x is 0, 1, 2, or 3. The catalyst may be dimethylformamide, (chloromethylene)dimethyliminium chloride, or triethylamine, among others. The chloro-substituted silane formed in the reaction along with several by-products has the formula $(R'O)_{4-x-y}SiR_xCl_y$; where x is 0, 1, 2, or 3 and y is 1, 2, 3, or 4. One of the by-products of the reaction is an alkyl chloride.

9 Claims, 4 Drawing Sheets

(56) References Cited

U.S. PATENT DOCUMENTS 5,679,823 A * 10/1997 Steiner .................... C07F 7/16
        556/472
5,716,590 A    2/1998 Roewer et al.
6,887,448 B2   5/2005 Block et al.

OTHER PUBLICATIONS

Shin Masaoka et al., Journal of Organometallic Chemistry, 691, Is. 1-2, Jan. 1, 2006, pp. 174-181 See pp. 175-176.

* cited by examiner

US 9,731,975 B2

ALTERNATIVE METHODS FOR THE SYNTHESIS OF ORGANOSILICON COMPOUNDS

CROSS REFERENCE TO RELATED APPLICATIONS

This application is the National Stage of International Application Serial No. PCT/US2012/029402 filed on Mar. 16, 2012, designating the United States and published in English, the entire contents of which is hereby incorporated herein by reference. International Application Serial No. PCT/US2012/029402 claims priority to European Patent Application No. 12159739.7 filed on Mar. 15, 2012.

FIELD

This disclosure relates generally to alternative methods of forming chloro-substituted silanes. More specifically, this disclosure relates to the reaction of alkoxysilanes with a chlorinating agent in the optional presence of a catalyst to form chloro-substituted silanes and alkyl chlorides, such as silicon tetrachloride and methyl chloride.

BACKGROUND

There currently exist many industrial uses of silicon tetrachloride ($SiCl_4$). For example, $SiCl_4$ is used in making high-surface area (fumed) silica, in the production of pure polycrystalline silicon used in the photovoltaic industry, and in the formation of very pure single-crystal silicon used in the semiconductor industry. Silicon tetrachloride is also used in the manufacturing process for optical fibers.

Conventionally, silicon tetrachloride has been made by several different reaction pathways, including (i) the reaction of silica with carbon and chlorine; (ii) the reaction of pyrolyzed rice hulls (which are rich in silica) with chlorine and carbon; (iii) the reaction of silicon carbide with chlorine; and (iv) the reaction between silica, silicon carbide and chlorine. Another route for forming silicon tetrachloride is to react tetraethylsilane with aluminum trichloride. In addition, technical grade $SiCl_4$ is made industrially by treating metallurgical silicon with hydrochloric acid. Very pure $SiCl_4$ is made industrially by the careful distillation of technical grade $SiCl_4$.

In each of the reactions indicated above, a very large amount of energy is used in making silicon by the carbothermic reduction of silica. Thus conventional routes to forming silicon tetrachloride require an undesirably large amount of energy. In addition, some conventional routes to silicon tetrachloride suffer from low yields and the use of expensive materials in the construction of reactors that can withstand aggressive or severe reaction conditions, as well as the presence of other engineering challenges.

SUMMARY

In overcoming the enumerated drawbacks and other limitations of the related art, the present disclosure provides a method of preparing chloro-substituted silanes. The method generally comprises the steps of providing an alkoxysilane, a chlorinating agent, and a catalyst; allowing the alkoxysilane to react with the chlorinating agent in the presence of the catalyst to form chloro-substituted silanes along with multiple by-products; and separating the chloro-substituted silanes from the by-products. The alkoxysilane has the formula $(R'O)_{4-x}SiR_x$, where R and R' are independently selected alkyl groups comprising one or more carbon atoms and x is 0, 1, 2, or 3. The chloro-substituted silanes formed by the reaction have the formula $(R'O)_{4-x-y}SiR_xCl_y$; where x is 0, 1, 2, or 3; y is 1, 2, 3, or 4; and one of the by-products is an alkyl chloride. The method may further comprise the step of separating the alkyl chloride from the by-products.

According to one aspect of the present disclosure, the catalyst is one selected from the group of dimethylformamide, dimethylacetamide, pyridine, triethylamine, (chloromethylene)dimethyliminium chloride, and mixtures thereof. The alkyl groups, R and R', are selected to be a methyl group, an ethyl group, a propyl group, a butyl group, an aryl group, such as a phenyl group or a mixture of two or more said groups. The chlorinating agent may be one selected from the group of thionyl chloride, sulfuryl chloride, phosphorus oxychloride, phosphorus trichloride, phosphorus pentachloride, and mixtures of two or more of said chlorinating agents. Alternatively, the chlorinating agent is thionyl chloride. The chlorinating agent may be provided in an amount that is greater than the stoichiometric amount necessary to completely react with the amount of alkoxysilane provided. The reaction between the alkoxysilane and the chlorinating agent is performed using at least one selected from the group of i) a temperature from 5° C. to 300° C., ii) a predetermined time up to 168 hours, and iii) a pressure that is equal to or greater than atmospheric pressure and less than or equal to 34 atmospheres (500 psi). The chloro-substituted silanes may include at least 50 wt. % or more silicon tetrachloride.

According to another aspect of the present disclosure, a method of preparing chloro-substituted silanes is provided in which the method comprises the steps of providing an alkoxysilane; providing hydrogen chloride as a chlorinating agent; allowing the alkoxysilane to react with the hydrogen chloride to form chloro-substituted silanes along with multiple by-products; and separating the chloro-substituted silanes from the by-products. The alkoxysilanes have the formula $(R'O)_{4-x}SiR_x$, where R and R' are independently selected alkyl group comprising one or more carbon atoms and x is 0, 1, 2, or 3. Alternatively, the alkyl groups are one selected from a methyl group, an ethyl group, a propyl group, a butyl group, and mixtures of two or more of said groups. The chloro-substituted silanes have the formula $(R'O)_{4-x-y}SiR_xCl_y$; where x is 0, 1, 2, or 3; y is 1, 2, 3, or 4; and one of the by-products is an alkyl chloride. Alternatively, the chloro-substituted silanes include at least 50 wt. % or more of silicon tetrachloride. The method may further comprise the step of separating the alkyl chloride from the by-products. The hydrogen chloride may be a liquid, a gas, or an aqueous solution.

The method may further comprise the steps of providing a second chlorinating agent and allowing the second chlorinating agent to react with the alkoxysilane along with the hydrogen chloride to form the chloro-substituted silanes. The second chlorinating agent is one selected from the group of thionyl chloride, sulfuryl chloride, phosphorus oxychloride, phosphorus trichloride, and mixtures of two or more of these chlorinating agents According to yet another aspect of the present disclosure, a method of preparing silicon tetrachloride is provided in which the method comprises providing tetraacetoxysilane, a chlorinating agent, and a catalyst; allowing the tetraacetoxysilane to react with the chlorinating agent in the presence of the catalyst to form silicon tetrachloride and by-products; and separating the silicon tetrachloride from the by-products. The chlorinating agent is one selected from the group of thionyl chloride, sulfuryl chloride, phosphorus oxychloride, phosphorus trichloride, and mixtures of two or more of said chlorinating agents. The catalyst is one selected from the group of dimethylformamide, dimethylacetamide, pyridine, triethylamine, (chloromethylene)-dimethyliminium chloride, and mixtures of two or more of said catalysts. The chlorinating agent may be present in an amount that is greater than the stoichiometric amount necessary to completely react with the amount of tetraacetoxysilane provided.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figure 1:
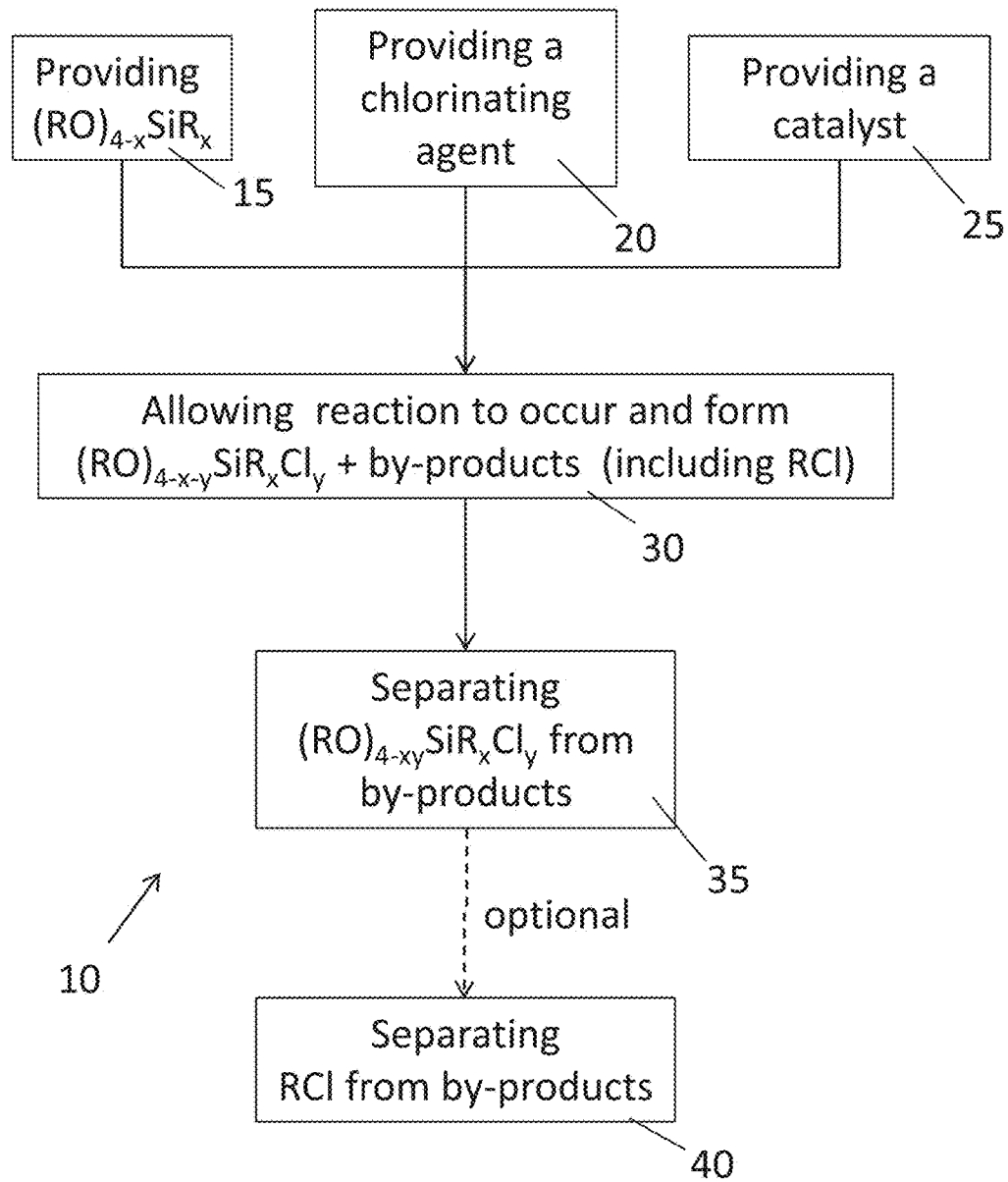
FIG. 1 is a schematic representation of a method of preparing chloro-substituted silanes according to one aspect of the present disclosure.

The following description is merely exemplary in nature and is in no way intended to limit the present disclosure or its application or uses. It should be understood that throughout the description, corresponding reference numerals indicate like or corresponding parts and features.

The present invention generally relates to a method of preparing chloro-substituted silanes from the reaction of a silane containing alkoxy or acetoxy functionality with a chlorinating agent under mild conditions. In addition to chloro-substituted silanes, the reaction may also form multiple by-products from which the chloro-substituted silanes can be separated. Alternatively, the reaction between the chlorinating agent and the silane's alkoxy or acetoxy groups may be facilitated by the presence of a catalyst.

Referring now to FIG. 1, the method 10 for preparing chloro-substituted silanes includes the steps of providing 15 an alkoxysilane; providing 20 a chlorinating agent; providing 25 a catalyst; and allowing 30 the alkoxysilane to react with the chlorinating agent in the presence of the catalyst to form the chloro-substituted silanes along with multiple by-products, wherein one of the by-products is an alkyl chloride. Subsequently, the chloro-substituted silanes can be separated 35 from the by-products. Alternatively, the alkyl chloride may also be separated 40 from the other by-products that are formed. The alkoxysilane used in the reaction can be described according to the formula:

$$(R'O)_{4-x}SiR_x,$$

where R and R' are independently selected alkyl groups comprising one or more carbon atoms and x is an integer selected from 0, 1, 2, or 3. Alternatively, the alkyl groups, R and R', are independently selected to be a methyl group, an ethyl group, a propyl group, a butyl group, an aryl group, such as a phenyl group, or a mixture thereof. Alternatively, the alkyl groups are a methyl group, ethyl group, or mixture thereof. Several examples of alkoxysilanes include, but are not limited to, tetramethoxysilane, tetraethoxysilane, methyltrimethoxysilane, methyltriethoxysilane, ethyltrimethoxysilane, ethyltriethoxysilane, dimethyldimethoxysilane, dimethyldiethoxy-silane, phenytrimethoxysilane, methyltripropoxysilane, and methyltributoxysilane.

The chloro-substituted silanes prepared by this method 10 may be described according to the formula:

$$(R'O)_{4-x-y}Si R_x Cl_y,$$

where x is an integer having the value of 0, 1, 2, or 3 and y is an integer having the value of 1, 2, 3, or 4. Alternatively, x is 0 and y is 4. Several examples of chloro-substituted silanes include, but are not limited to, silicon tetrachloride, methyltrichlorosilane, ethyltrichlorosilane, phenyltrichlorosilane, chlorotrimethoxysilane, dichlorodimethoxysilane, trichloromethoxysilane, chloromethyldimethoxysilane, and dichloromethylmethoxysilane, among others.

The chlorinating agent may be selected as one from the group of thionyl chloride ($SOCl_2$), sulfuryl chloride ($SO_2Cl_2$), phosphorus oxychloride ($POCl_3$), phosphorus trichloride ($PCl_5$), phosphorus pentachloride ($PCl_5$), hydrogen chloride (HCl), and mixtures thereof. Alternatively, the chlorinating agent is thionyl chloride, hydrogen chloride, or a mixture thereof. The hydrogen chloride may be either in liquid or gaseous form. The chlorinating agent may be provided in any desired amount with an amount equivalent to or greater than the stoichiometric amount necessary to react with the alkoxysilanes providing the greatest conversion of the alkoxysilanes to chloro-substituted silanes. As referred to herein, the term stoichiometric amount refers to the number of moles of each reactant taking part in the reaction according to a balanced chemical equation. Optionally, between a 2-fold and 8-fold excess of the chlorinating agent may be utilized. Alternatively, the excess above the stoichiometric amount of the chlorinating agent is 4-fold. Another way of referring to an excess of the chlorinating agent is to describe a molar ratio of chlorinating agent to alkoxysilane to be greater than 1/1. Alternatively, the molar ratio of chlorinating agent to alkoxysilane is between 2/1 and 32/1.

The catalyst may be selected as one from the group of benzene, quinolone, 2,3,5-collidine, cyanuric chloride, trimethylamine, triethylamine, butylamine, dibutylamine, tributylamine, dimethylformamide, dimethylacetamide, pyridine, dimethylaniline, 2-imidazolidone, 1,3-dimethyl-2-imidazolidone, (chloromethylene)-dimethyliminium chloride, N-chlorosuccinimide, zinc chloride, and mixtures thereof. Alternatively, the catalyst is selected as one from the group of dimethylformamide, dimethylacetamide, triethylamine, (chloromethylene)dimethyliminium chloride, and mixtures thereof. Alternatively, the catalyst is dimethylformamide (DMF). The molar ratio of catalyst to alkoxysilane may range from about 0.05/1 to about 1/1.

The reaction between the alkoxysilane and the chlorinating agent in the optional presence of a catalyst occurs under predetermined conditions of temperature, pressure, and time. The actual conditions may be determined based on a balancing of multiple manufacturing parameters, which include but are not limited to product cost, overall reaction yield, and desirable product composition or distribution. More specifically, the reaction time may include any time period up to about 168 hours. Generally, allowing more time for the reaction to occur increases the relative amount of chlorine substitution in the alkoxysilanes. Alternatively, the reaction time is selected to be within the range of about 0.1 to 72 hours. The temperature of the reaction may range from a low temperature, such as 5° C. when desirable, up to about 300° C. Due to the volatility of the reactants, the pressure of the vessel in which the reaction occurs is selected to be atmospheric pressure or above. Alternatively, the pressure is selected to be within the range of atmospheric pressure up to about 34 atmospheres (~500 psi). The chlorosilanes and any alkylchloride by-product produced in the reaction can be purified and separated from the starting materials in the reaction using any method of distillation known to one skilled in the art.

The following examples and compositions are provided to more fully illustrate the formation of chloro-substituted silanes from the reaction of an alkoxysilane and a chlorinating agent in the presence of a catalyst, but are not intended to limit the scope of the present disclosure. One skilled in the art will understand that the use of other analogous materials and procedures than those described in the examples may be used without exceeding the scope of the present disclosure.

Multiple reactions (Run No.'s 1-20) are provided that demonstrate the reaction of tetramethoxysilane with thionyl chloride at ambient temperature and atmospheric pressure in the presence of various catalysts. In these reactions, the molar ratio of the chlorinating agent to tetramethoxysilane used is 16/1, a 4-fold excess, or 4/1 (a stoichiometric ratio), while the molar ratio of the catalyst to tetramethoxysilane is either 0.05/1 or 0.2/1. The relative intensity of the chloro-substituted silanes produced from each reaction at various reaction times is provided in Table 1. The relative product intensity is determined through the analysis of $^{29}$Si nuclear magnetic resonance (NMR) spectra with an intensity of 10 being the most intense.

TABLE 1

| Run No. | Catalyst | Ratio Agent to Silane | Ratio Catalyst to Silane | Reaction Time (hours) | RELATIVE INTENSITY OF PRODUCTS | | | |
|---|---|---|---|---|---|---|---|---|
| | | | | | $Si(OCH_3)_3Cl$ | $Si(OCH_3)_2Cl_2$ | $Si(OCH_3)Cl_3$ | $SiCl_4$ |
| 1 | benzene | 16/1 | 0.2/1 | 48 | 10 | 8 | — | — |
| 2 | pyridine | 16/1 | 0.2/1 | 48 | — | — | — | 10 |
| 3 | pyridine | 4/1 | 0.05/1 | 48 | | — | 8 | 10 |
| 4 | quinoline | 16/1 | 0.2/1 | 48 | — | — | — | 10 |
| 5 | quinoline | 4/1 | 0.05/1 | 48 | | | 10 | 7 |
| 6 | 2,3,5-collidine | 16/1 | 0.2/1 | 48 | — | — | — | 10 |
| 7 | triethylamine | 16/1 | 0.2/1 | 2 | 3 | 10 | — | — |
| 8 | dimethylformamide | 16/1 | 0.2/1 | 0.5 | — | 10 | 4 | — |
| 9 | dimethylformamide | 4/1 | 0.05/1 | 0.5 | 4 | 10 | 1 | |
| 10 | dimethylformamide | 16/1 | 0.2/1 | 3 | — | 4 | 10 | 7 |
| 11 | dimethylformamide | 16/1 | 0.2/1 | 48 | — | — | — | 10 |
| 12 | dimethylformamide | 4/1 | 0.05/1 | 48 | | 4 | 10 | 2 |
| 13 | dimethylacetamide | 16/1 | 0.2/1 | 3 | — | 4 | 10 | 7 |
| 14 | dimethylacetamide | 4/1 | 0.05/1 | 48 | — | — | 10 | 6 |
| 15 | 2-imidazolidone | 16/1 | 0.2/1 | 0.5 | 2 | 10 | 3 | — |
| 16 | 2-imidazolidone | 16/1 | 0.2/1 | 48 | — | — | 10 | 8 |
| 17 | 1,3-dimethyl-2-imidazolidone | 16/1 | 0.2/1 | 0.5 | — | 4 | 10 | 3 |
| 18 | 1,3-dimethyl-2-imidazolidone | 4/1 | 0.05/1 | 0.5 | 1 | 10 | 4 | — |
| 19 | iminium chloride | 16/1 | 0.2/1 | 2 | — | 5 | 10 | 7 |
| 20 | zinc chloride | 16/1 | 0.2/1 | 48 | — | 10 | — | — |

In Run No.'s 1-20, a chloro-substituted silane or a mixture of chloro-substituted silanes is produced from the reaction between an alkoxysilane and a chlorinating agent with the formation of tetrachlorosilane being identified in Run No.'s 2-6, 10-14, 16, 17, and 19. An increase in the number of chloro groups present in the chloro-substituted silane occurs with an increase in reaction time (e.g., compare Run No.'s: 8 with 10-11; and 15 with 16). The reaction shown in Run No. 11 is summarized in Equation 1, where thionyl chloride is shown to react with tetramethoxysilane in the presence of dimethylformamide to form silicon tetrachloride, methyl chloride, and sulfur dioxide.

$$Si(OCH_3)_4 + 4\ SOCl_2 \xrightarrow{DMF} SiCl_4 + 4\ CH_3Cl + 4\ SO_2 \quad \text{(Eq. 1)}$$

Different chlorinating agents provide similar results when reacted with an alkoxysilane under identical conditions of temperature and pressure. For example, the use of $SO_2Cl_2$, $PCl_5$, and $POCl_3$ (Run No.'s 21-28) is compared against the use of $SOCl_2$ (see Table 1, Run No.'s 8, 10 and 11) as the chlorinating agent in Table 2. In each of these reactions (Run No.'s 21-28), the chlorinating agent is reacted with tetramethoxysilane at ambient temperature and atmospheric pressure. The mole ratio of chlorinating agent to silane in each of these reactions is 16/1, while the molar ratio of catalyst to silane is 0.2/1. The relative intensity of the chloro-substituted silanes produced from each reaction at various reaction times is also provided in Table 2. Run No. 25 provides further demonstration of the formation of tetrachlorosilane using phosphorus trichloride as the chlorinating agent in the presence of a dimethylformamide catalyst.

TABLE 2

| Run No. | Chlorinating Agent | Chlorinating Agent | Reaction Time (hours) | RELATIVE INTENSITY OF PRODUCTS | | | |
|---|---|---|---|---|---|---|---|
| | | | | $Si(OCH_3)_3Cl$ | $Si(OCH_3)_2Cl_2$ | $Si(OCH_3)Cl_3$ | $SiCl_4$ |
| 21 | butylamine | $SO_2Cl_2$ | 48 | 3 | 10 | 6 | — |
| 22 | triethylamine | $SO_2Cl_2$ | 48 | — | 6 | 7 | — |
| 23 | dimethylformamide | $SO_2Cl_2$ | 48 | — | — | 10 | — |
| 24 | dimethylformamide | $PCl_3$ | 2 | 10 | 6 | | — |
| 25 | dimethylformamide | $PCl_3$ | 48 | 1 | 10 | 5 | 2 |
| 26 | inimium chloride | $PCl_3$ | 48 | — | 10 | 6 | — |
| 27 | triethylamine | $POCl_3$ | 72 | — | 10 | 4 | — |
| 28 | dimethylformamide | $POCl_3$ | 48 | 1 | 10 | 4 | — |
| 29 | inimium chloride | $POCl_3$ | 48 | 2 | 10 | 3 | — |

In addition to the catalyzed conversion of a tetraalkoxysilane to a chloro-substituted silane as described in Equation 1, other alkoxysilanes described by the formula $(R'O)_{4-x}SiR_x$, where R and R' are independently selected alkyl groups and x is 1, 2, or 3 may be used. For example, $(CH_3)_3Si(OCH_3)$, $(CH_3)_2Si(OCH_3)_2$, and $(CH_3)Si(OCH_3)_3$ can react with a chlorinating agent, such as thionyl chloride, in the presence of a catalyst to yield chloro-substituted silanes, methyl chloride, and sulfur dioxide as described in Equations 2-4. The Si—$OCH_3$ bond present in these methylmethoxysilanes is readily displaced by a Si—Cl bond under mild conditions. One skilled in the art will understand that other alkyl groups, such as ethyl groups, among others, may be utilized without exceeding the scope of the present disclosure. The substitution of the methoxy groups present in the silane with ethoxy groups will provide similar chlorination results.

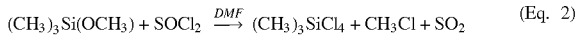  (Eq. 2)

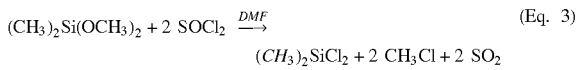  (Eq. 3)

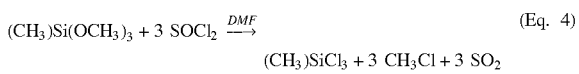  (Eq. 4)

In Run No.'s 30-35, reactions are performed according to Equation 2 (Run No. 30), Equation 3 (Run No. 32), and Equation 4 (Run No. 34). For comparison, similar reactions (Run No.'s 31, 33, and 35) are conducted in which the methoxy groups present in the methylmethoxysilanes are substituted with ethoxy groups. Each of the reactions (Run No.'s 30-35) are performed under similar conditions. More specifically, an excess of $SOCl_2$ is utilized, such that the molar ratio of $SOCl_2$ to silane is 16/1. In addition, each of the runs is conducted under atmospheric pressure and at an elevated temperature of 55° C. with the molar ratio of dimethylformamide (DMF) to silane being 0.4/1. The yield of chloro-substituted silanes from these reactions is on the order of greater than about 50 wt. %; alternatively greater than about 60 wt. %. Very little to no difference in the yield of the chloro-substituted silane is observed between methylalkoxysilanes in which the alkoxy groups are methoxy groups (Run No.'s 30, 32, and 34) or ethoxy groups (Run No.'s 31, 33, and 35).

TABLE 3

| Run No. | Alkylalkoxysilane | Chloro-substituted Silane | Reaction Time (hours) | Yield of Choro-substituted Silane |
|---|---|---|---|---|
| 30 | $(CH_3)_3Si(OCH_3)$ | $(CH_3)_3SiCl$ | 0.5 | 75% |
| 31 | $(CH_3)_3Si(OCH_2CH_3)$ | $(CH_3)_3SiCl$ | 0.5 | 60% |
| 32 | $(CH_3)_2Si(OCH_3)_2$ | $(CH_3)_2SiCl_2$ | 0.5 | 60% |
| 33 | $(CH_3)_2Si(OCH_2CH_3)_2$ | $(CH_3)_2SiCl_2$ | 0.5 | 60% |
| 34 | $(CH_3)Si(OCH_3)_3$ | $(CH_3)SiCl_3$ | 2 | 60% |
| 35 | $(CH_3)Si(OCH_2CH_3)_3$ | $(CH_3)SiCl_3$ | 7 | 60% |

Multiple reactions (Run No.'s 36-47) conducted according to Equation 1 demonstrate the effect that various reaction variables, such as the ratio of $SOCl_2$ to tetramethoxysilane, the ratio of DMF to tetramethoxysilane, temperature, and time, can have on the overall yield of silicon tetrachloride obtained. In Run No.'s 36-37 and 38-39, a decrease in the molar ratio of chlorinating agent ($SOCl_2$) to tetramethoxysilane and the molar ratio of DMF to tetramethoxysilane gives both a lower yield of silicon tetrachloride and a longer reaction time. A similar effect of lowering the yield of silicon tetrachloride occurs upon reducing the reaction temperature as demonstrated by the comparison of Run No.'s 40-44. The overall yield may be maintained at a relatively constant level by increasing the reaction time. The same trend with respect to temperature is observed upon reducing the molar ratios of chlorinating agent to silane and catalyst to silane (e.g., compare Run No.'s 45-47 with Run No.'s 40-44).

TABLE 4

| Run No. | Variable Investigated | $SOCl_2/Si(OCH_3)_4$ ratio | $DMF/Si(OCH_3)_4$ ratio | Reaction Time (hours) | Temperature (° C.) | $SiCl_4$ Yield (%) |
|---|---|---|---|---|---|---|
| 36 | $SOCl_2/Si(OCH_3)_4$ ratio | 16/1 | 0.4/1 | 8 | 55 | 63 |
| 37 | and $DMF/Si(OCH_3)_4$ ratio | 8/1 | 0.2/1 | 17 | 55 | 43 |
| 38 | $DMF/Si(OCH_3)_4$ ratio | 16/1 | 0.4/1 | 8 | 55 | 63 |
| 39 | | 16/1 | 0.2/1 | 17 | 55 | 54 |
| 40 | Temperature | 16/1 | 0.4/1 | 8 | 55 | 63 |
| 41 | | 16/1 | 0.4/1 | 17 | 45 | 57 |

TABLE 4-continued

| Run No. | Variable Investigated | SOCl$_2$/Si(OCH$_3$)$_4$ ratio | DMF/Si(OCH$_3$)$_4$ ratio | Reaction Time (hours) | Temperature (° C.) | SiCl$_4$ Yield (%) |
|---|---|---|---|---|---|---|
| 42 | | 16/1 | 0.4/1 | 21 | 35 | 53 |
| 43 | | 16/1 | 0.4/1 | 25 | 35 | 53 |
| 44 | | 16/1 | 0.4/1 | 96 | 25 | 53 |
| 45 | Temperature | 8/1 | 0.1/1 | 28 | 55 | 50 |
| 46 | | 8/1 | 0.1/1 | 71 | 38 | 45 |
| 47 | | 8/1 | 0.1/1 | 168 | 25 | 48 |

Other catalyst formulations, as previously described above, can provide results that are similar to those obtained with dimethylformamide (DMF). As shown in Table 5, the substitution of the DMF catalyst (Run No. 36) with dimethylacetamide (Run No. 48), triethylamine (Run No.'s 49-50), or (chloromethylene)dimethyliminium chloride (Run No.'s 51-52) provides further demonstration that all of these catalysts are effective in forming silicon tetrachloride from the reaction between tetramethoxysilane and thionyl chloride. Each of these reactions (Run No.'s 36, 48-52) is conducted under similar conditions including a temperature of 55° C. and an excess of the chlorinating agent, SOCl$_2$. The yield of SiCl$_4$ formed in each reaction ranged from about 55% (Run No. 48) to 70% (Run No. 50). Although not wanting to be constrained by theory, it is believed that in Run No. 36, the SOCl$_2$ may react with DMF during the reaction to form the iminium chloride catalyst used in Run No's 51-52.

TABLE 5

| Run No. | Catalyst | SOCl$_2$ to Si(OCH$_3$)$_4$ ratio | Catalyst to Si(OCH$_3$)$_4$ ratio | Reaction Time (hours) | SiCl$_4$ Yield (%) |
|---|---|---|---|---|---|
| 36 | Dimethylformamide | 16/1 | 0.4/1 | 8 | 63 |
| 48 | Dimethylacetamide | 16/1 | 0.2/1 | 24 | 55 |
| 49 | Triethylamine | 16/1 | 0.4/1 | 32 | 64 |
| 50 | Triethylamine | 16/1 | 0.2/1 | 8 | 70 |
| 51 | (chloromethylene) dimethyliminium | 16/1 | 0.4/1 | 17 | 62 |
| 52 | (chloromethylene) dimethyliminium | 16/1 | 0.2/1 | 8 | 65 |

According to one aspect of the present disclosure, the yield of silicon tetrachloride may be increased through the use of low temperature traps on any vent line associated with chlorination apparatus that is in communication with the reaction mixture. The volatility of the silicon tetrachloride formed in the reaction results in a loss of SiCl$_4$ vapor through the vent line. The addition of a low temperature trap, including but not limited to an ice slurry trap, a dry ice/acetone slurry trap, a dry ice/carbon tetrachloride slurry, or a dry ice/acetonitrile trap, is capable of increasing the yield of silicon tetrachloride recovered from the reaction by about 15-30%. In other words, the yield of silicon tetrachloride from the reaction of tetramethoxysilane with thionyl chloride in the presence of a DMF catalyst can be increased from about 63% (Run No. 36) to about 78-92% through the use of a low temperature trap.

Several examples of reacting tetraalkoxysilanes with thionyl chloride in the presence of a DMF catalyst are provided in Run No.'s 53-56. In each of these runs, the molar ratio of thionyl chloride to silane is 16/1 and the molar ratio of DMF to silane is 0.4/1. Each run is conducted at atmospheric pressure and a reaction temperature of 55° C. The yield of SiCl$_4$ obtained in Run No.'s 53-56 at various reaction times is provided in Table 6. Overall the reaction time required to obtain a similar product yield increases with the larger alkoxy groups utilized.

TABLE 6

| Run No. | tetraalkoxysilane | SOCl$_2$ to silane ratio | DMF to silane ratio | Reaction Time (hours) | SiCl$_4$ Yield (%) |
|---|---|---|---|---|---|
| 53 | tetramethoxysilane | 16/1 | 0.4/1 | 8 | 63 |
| 54 | tetraethoxysilane | 16/1 | 0.4/1 | 15 | 43 |
| 55 | tetrapropoxysilane | 16/1 | 0.4/1 | 32 | 46 |
| 56 | tetrabutoxysilane | 16/1 | 0.4/1 | 64 | 73 |

Figure 2:
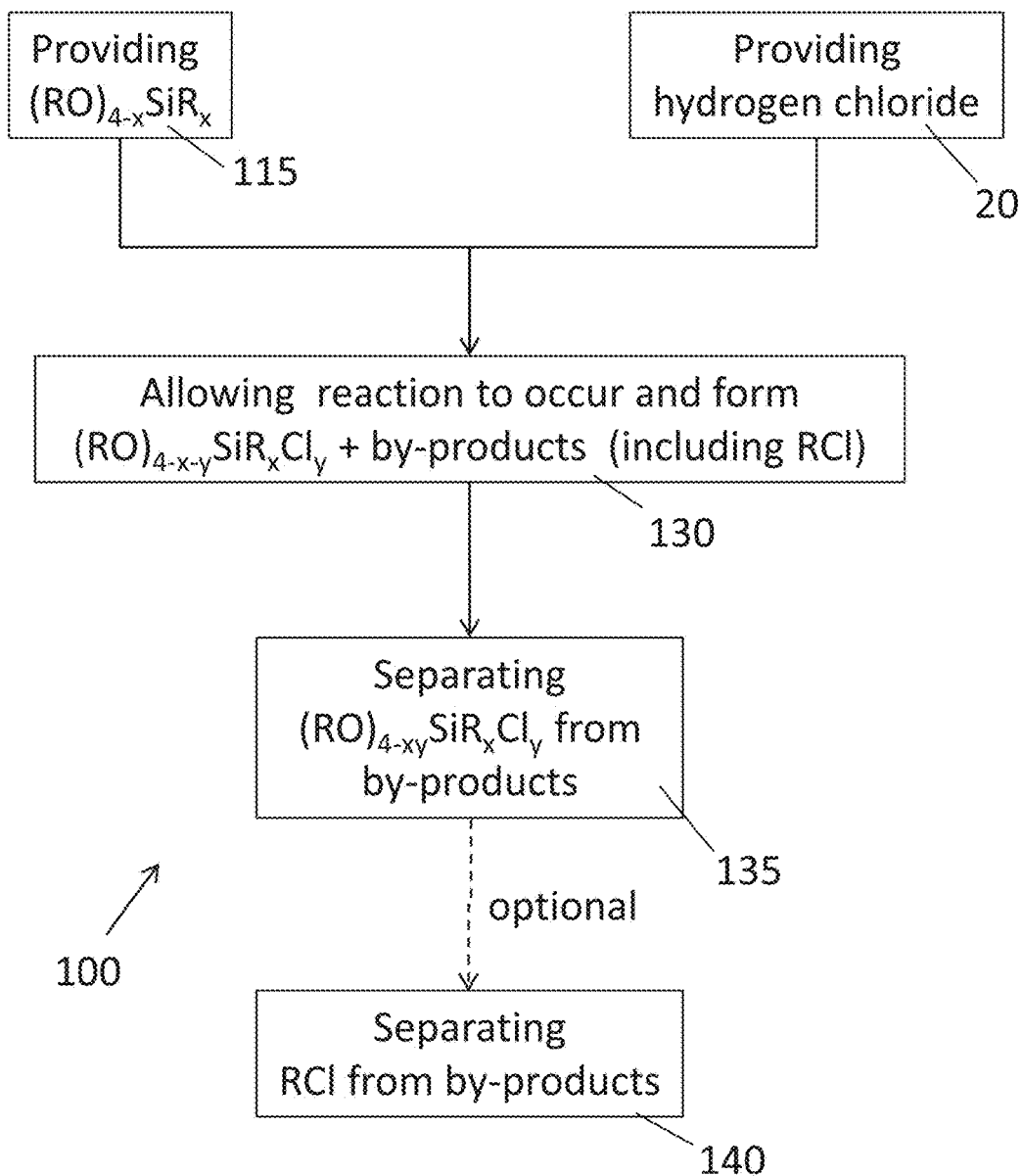
FIG. 2 is a schematic representation of a method of preparing chloro-substituted silanes according to another aspect of the present disclosure.

According to another aspect of the present disclosure, a method 100 is provided for forming chloro-substituted silanes Referring now to FIG. 2, the method 100 includes the steps of providing 115 an alkoxysilane as previously described; providing 120 hydrogen chloride as the chlorinating agent; and allowing 130 the alkoxysilane to react with the hydrogen chloride to form the previously described chloro-substituted silanes along with multiple by-products, wherein one of the by-products is an alkyl chloride. Subsequently, the chloro-substituted silanes can be separated 135 from the by-products. Alternatively, the alkyl chloride may also be separated 140 from the other by-products that are formed.

In Table 7, Run No.'s 57-60 demonstrate the formation of a chloro-substituted silane from the reaction of an alkoxysilane with hydrogen chloride under various reaction conditions. The hydrogen chloride may be a liquid, a gas, or an aqueous solution. In Run No. 57, the HCl is added at a rate of about 78 mL/min. The number of times of the stoichiometric amount of HCl ranged from 0.5 to 5, while the temperature at which the reaction occurred ranged from room temperature to less than −85° C. The amount of the chloro-substituted silane obtained in Run No.'s 57-58 is quantified by the relative intensity of the measured $^{29}$Si NMR resonance with 10 being the most intense.

TABLE 7

| Run No. | Alkylalkoxysilane | Chlorinating Agent | HCl to silane excess | Reaction Time (hours) | Temperature (° C.) | Chloro-substituted silane | Relative Intensity |
|---|---|---|---|---|---|---|---|
| 57 | (CH$_3$)$_3$Si(OCH$_3$) | 12N HCl$_{(aq)}$ | 5-fold | 3 | 0 | (CH$_3$)$_3$SiCl | 4 |
| 58 | (CH$_3$)Si(OCH$_3$)$_3$ | HCl$_{(g)}$ | 2-fold | 1 | RT | (CH$_3$)Si(OCH$_3$)$_2$Cl | 10 |

TABLE 7-continued

| Run No. | Alkylalkoxysilane | Chlorinating Agent | HCl to silane excess | Reaction Time (hours) | Temperature (° C.) | Chloro-substituted silane | Relative Intensity |
|---|---|---|---|---|---|---|---|
| 59 | Si(OCH$_3$)$_4$ | HCl$_{(g)}$ | 0.8-fold | 0.5 | RT | Si(OCH$_3$)$_3$Cl | 7 |
| 60 | Si(OCH$_3$)$_4$ | HCl$_{(l)}$ | 0.5-fold | 0.3 | <−85 | Si(OCH$_3$)$_3$Cl | 10 |

Figure 3:
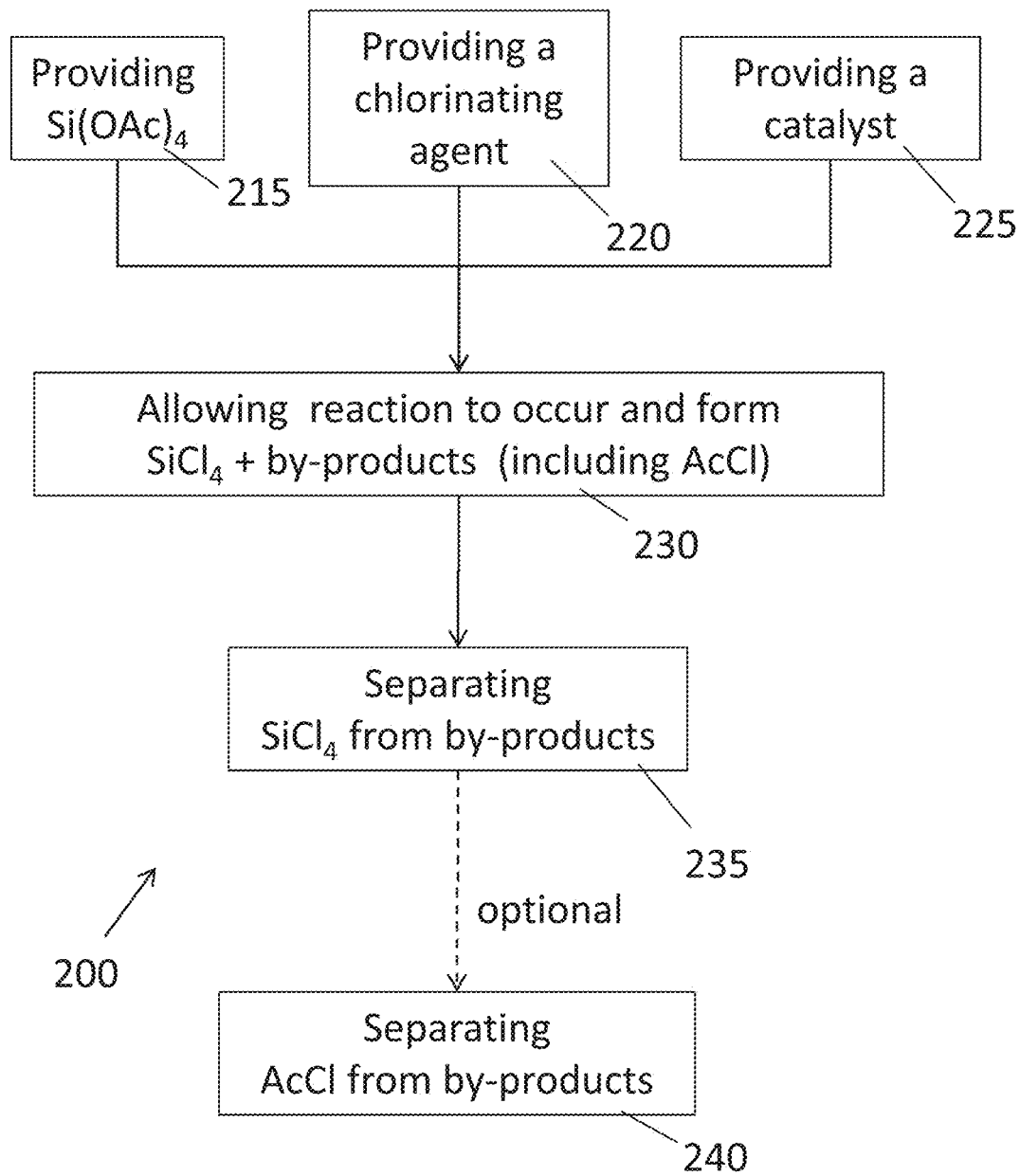
FIG. 3 is a schematic representation of a method of preparing chloro-substituted silanes according to yet another aspect of the present disclosure.

According to another aspect of the present disclosure, a method 200 of preparing silicon tetrachloride is provided. Referring now to FIG. 3, this method 200 comprises the steps of providing 215 tetraacetoxyysilane; providing 220 a chlorinating agent; and providing 225 a catalyst. The tetraacetoxysilane is then allowed 230 to react with the chlorinating agent in the presence of the catalyst to form the silicon tetrachloride and by-products. Finally, the silicon tetrachloride is separated 235 from the by-products. Optionally, the acetyl chloride formed during the reaction can be separated 240 from the other by-products of the reaction.

One specific example of this method 200 is described by Equation 5, wherein the chlorinating agent is thionyl chloride and the catalyst is dimethylformamide (DMF). In this reaction, the thionyl chloride reacts with tetraacetoxysilane in the presence of DMF to form the silicon tetrachloride, sulfur dioxide, and acetyl chloride (AcCl). The fact that the reaction of tetraacetoxysilane and thionyl chloride can be catalyzed by dimethylformamide parallels the reaction of tetramethoxysilane and thionyl chloride in the presence of dimethylformamide (see Eq. 1). Other catalysts, such as pyridine, PCl$_5$ and CHCl$_3$ may be used instead of DMF.

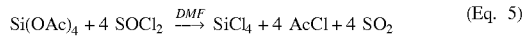

$$Si(OAc)_4 + 4\ SOCl_2 \xrightarrow{DMF} SiCl_4 + 4\ AcCl + 4\ SO_2 \qquad (Eq.\ 5)$$

The occurrence of the reaction described in Equation 5 is demonstrated in Run No.'s 61-64 using various catalysts. As shown in Table 8, the reaction conducted at atmospheric pressure and a temperature of 120° C. using a molar ratio of catalyst to tetraacetoxysilane of about 0.02/1 to 0.05/1 and a molar ratio of thionyl chloride to tetraacetoxysilane of 50/1 produces a high yield of silicon tetrachloride. The temperature of 120° C. or more is chosen so as to have a temperature that is above the melting point of the tetraacetoxysilane. The relative intensity of the $^{29}$Si NMR resonance measured for the silicon tetrachloride obtained in Run No.'s 61-63 is the maximum of 10. Thus dimethylformamide (Run No. 61), pyridine (Run No. 62), and CH$_3$Cl (Run No. 63) are each effective as a catalyst for the reaction of tetraacetoxysilane with SOCl$_2$ as depicted in Equation 5.

TABLE 8

| Run No. | Catalyst | Catalyst to Si(OAc)$_4$ | SOCl$_2$ to Si(OAc)$_4$ | Reaction Time (hours) | Temperature (° C.) | Relative Intensity of SiCl$_4$ |
|---|---|---|---|---|---|---|
| 61 | dimethylformamide | 0.03/1 | 50/1 | 0.2 | 120 | 10 |
| 62 | pyridine | 0.025/1 | 50/1 | 0.2 | 120 | 10 |
| 63 | CHCl$_3$ | 0.026/1 | 50/1 | 0.2 | 120 | 10 |

The following specific examples are given to further illustrate the preparation of chloro-substituted silanes according to the teachings of the present disclosure and should not be construed to limit the scope of the disclosure. Those skilled-in-the-art, in light of the present disclosure, will appreciate that many changes can be made in the specific embodiments which are disclosed herein and still obtain alike or similar result without departing from or exceeding the spirit or scope of the disclosure.

The commercial reagents and solvents used in these examples are generally of reagent grade quality or better. Most of the organosilicon reagents may be purchased from commercial sources, such as Gelest. Tullytown, Pa. and Aldrich, Milwaukee, Wis., and most of the organic reagents may be purchased from reagent chemical vendors (e.g., Aldrich, Gelest, and Fisher Scientific, Pittsburgh, Pa.). Typically the glassware used in each example is oven-dried (110° C.) for 24 hours and then cooled in the atmosphere prior to use.

Example 1—Reaction of Tetramethoxysilane with Excess Thionyl Chloride in the Presence of a Catalyst In Run No.'s 1, 2, 4, 6-8, 10, 11, 13, 15-17, 19, and 20, a solution of tetramethoxysilane, thionyl chloride, and a catalyst as described in Table 1 is prepared with a SOCl$_2$ to silane molar ratio of 16/1 (4-fold excess) and a catalyst to silane ratio of 0.2/1. The amount of tetramethoxysilane, thionyl chloride, and catalyst used to prepare each solution is provided in Table 9. The solution is allowed to stand in a vial at room temperature for 48 hours. Samples of the mixture in each run are taken at 0.5 hour and at the end of the run (e.g., 48 hours). The composition of each mixture was analyzed using $^{29}$Si nuclear magnetic resonance with the intensity for any chloro-substituted silanes formed being numerically recorded on a scale from 1 to 10 with the 10 representing the maximum intensity.

TABLE 9

| Run No. | Tetramethoxysilane | | Thionyl Chloride | | Catalyst | |
|---|---|---|---|---|---|---|
| | volume (mL) | mmol | volume (mL) | mmol | μL | grams |
| 1 | 0.13 | 0.85 | 1.0 | 14 | 16 | — |
| 2 | 0.13 | 0.85 | 1.0 | 14 | 14 | — |

TABLE 9-continued

| Run No. | Tetramethoxysilane volume (mL) | mmol | Thionyl Chloride volume (mL) | mmol | Catalyst µL | grams |
|---|---|---|---|---|---|---|
| 4 | 0.13 | 0.85 | 1.0 | 14 | 21 | — |
| 6 | 0.13 | 0.85 | 1.0 | 14 | 23 | — |
| 7 | 0.26 | 1.7 | 2.0 | 27 | 50 | — |
| 8 | 0.13 | 0.85 | 1.0 | 14 | 14 | — |
| 10 | 0.26 | 1.7 | 2.0 | 27 | 28 | — |
| 11 | 0.13 | 1.7 | 2.0 | 27 | 14 | — |
| 13 | 0.26 | 1.7 | 2.0 | 27 | 17 | — |
| 15 | 0.26 | 1.7 | 2.0 | 27 | — | 0.03 |
| 16 | 0.26 | 1.7 | 2.0 | 27 | — | 0.03 |
| 17 | 0.26 | 1.7 | 2.0 | 27 | 38 | — |
| 19 | 0.26 | 1.7 | 2.0 | 27 | — | 0.04 |
| 20 | 0.13 | 0.85 | 1.0 | 14 | 16 | — |

Example 2—Reaction of Tetramethoxysilane with a Stoichiometric Amount of Thionyl Chloride in the Presence of a Catalyst In Run No.'s 3, 5, 9, 12, 14, and 18, a solution of tetramethoxysilane, thionyl chloride, and a catalyst as described in Table 1 is prepared with a SOCl₂ to silane molar ratio of 4/1 (stoichiometric amount) and a catalyst to silane ratio of 0.05/1. The amount of tetramethoxysilane, thionyl chloride, and catalyst used to prepare each solution is provided in Table 10. The solution is allowed to stand in a vial at room temperature for 48 hours. Samples of the mixture in each run are taken at 0.5 hour and at the end of the run (e.g., 48 hours). The composition of each mixture was analyzed using $^{29}$Si nuclear magnetic resonance with the intensity for any choro-substituted silanes formed being recorded on a scale of 1-10 with a 10 representing the maximum intensity.

TABLE 10

| Run No. | Tetramethoxysilane volume (mL) | mmol | Thionyl Chloride volume (mL) | mmol | Catalyst µL | grams |
|---|---|---|---|---|---|---|
| 3 | 0.51 | 3.4 | 1.0 | 14 | 14 | — |
| 5 | 0.51 | 3.4 | 1.0 | 14 | 21 | — |
| 9 | 0.51 | 3.4 | 1.0 | 14 | 14 | — |
| 12 | 0.51 | 3.4 | 1.0 | 14 | 14 | — |
| 14 | 0.51 | 3.4 | 1.0 | 14 | 17 | — |
| 18 | 1.1 | 7.1 | 2.0 | 27 | 38 | — |

Example 3—Reaction of Tetramethoxysilane with Excess Amount of SO₂Cl₂, PCl₃, or POCl₃ in the Presence of a Catalyst In Run No.'s 21-29, a solution of tetramethoxysilane, a chlorinating agent (SO₂Cl₂, PCl₃, or POCl₃), and a catalyst as described in Table 2 is prepared with a chlorinating agent to silane molar ratio of 16/1 (a 4-fold excess) and a catalyst to silane ratio of 0.2/1. In Run #23, the catalyst to silane ratio was increased to 0.4/1. The amount of tetramethoxysilane, chlorinating agent, and catalyst used to prepare each solution is provided in Table 11. The solution is allowed to stand in a vial at room temperature for 48 hours. Samples of the mixture in each run are taken at 0.5 hour and at the end of the run (e.g., 48 hours). The composition of each mixture was analyzed using $^{29}$Si nuclear magnetic resonance with the intensity for any choro-substituted silanes formed being recorded on a scale from 1 to 10 with a 10 representing the maximum intensity.

TABLE 11

| Run No. | Tetramethoxysilane volume (mL) | mmol | Chorinating Agent volume (mL) | mmol | Catalyst µL | grams |
|---|---|---|---|---|---|---|
| 21 | 0.26 | 1.7 | 2.2 | 27 | 35 | — |
| 22 | 0.26 | 1.7 | 2.2 | 27 | 50 | — |
| 23 | 0.26 | 1.7 | 2.2 | 27 | 56 | — |
| 24 | 0.26 | 1.7 | 2.4 | 27 | 28 | — |
| 25 | 0.26 | 1.7 | 2.4 | 27 | 28 | — |
| 26 | 0.26 | 1.7 | 2.4 | 27 | — | 0.04 |
| 27 | 0.26 | 1.7 | 2.5 | 27 | 50 | — |
| 28 | 0.26 | 1.7 | 2.5 | 27 | 28 | — |
| 29 | 0.26 | 1.7 | 2.5 | 27 | — | 0.04 |

Example 4—Preparation of Chloro-Substituted Silanes from Alkoxysilanes and Excess Thionyl Chloride in the Presence of a Dimethylformamide Catalyst In Run No.'s 30-35, a warmed (55° C.) mixture of an alkoxysilane, thionyl chloride, and dimethylformamide (DMF) as described in Table 3 is prepared with a catalyst to silane ratio of 0.4/1. The molar ratio of thionyl chloride to silane in Run No.'s 30-35 is 16/1; which for Run No.'s 30-31 is a 4-fold excess, for Run No's 32-33 is an 8-fold excess, and for Run No.'s 34-35 is a 5.3-fold excess. The amount of alkoxysilane, thionyl chloride, and DMF used to prepare each mixture is provided in Table 12. The warmed mixture is refluxed for 0.5 hours in each run with the exception that the reflux time in Run No.'s 34 and 35 are 2 hours and 7 hours, respectively. The reaction mixture is fractionally distilled at atmospheric pressure using a 29 cm column with glass helices packing. However, due to the closeness in boiling points of the materials involved in each run, the determination of composition and % yield by fractional distillation is difficult. Only in Run No. 30 is it possible to determine the composition and % yield of the chloro-substituted silanes produced from the distillate collected, Thus in each run, the composition and percent yield of the chloro-substituted silanes are determined on the basis of the relative intensity of the resonances measured using $^{29}$Si NMR spectroscopy.

TABLE 12

| Run No. | Alkylalkoxysilane Composition | volume (mL) | mmol | Thionyl Chloride volume (mL) | mmol | DMF volume (mL) |
|---|---|---|---|---|---|---|
| 30 | (CH₃)₃Si(OCH₃) | 11.8 | 0.086 | 100 | 1.37 | 2.75 |
| 31 | (CH₃)₃Si(OCH₂CH₃) | 13.4 | 0.086 | 100 | 1.37 | 2.75 |
| 32 | (CH₃)₂Si(OCH₃)₂ | 11.9 | 0.087 | 100 | 1.37 | 2.75 |
| 33 | (CH₃)₂Si(OCH₂CH₃)₂ | 15.1 | 0.088 | 100 | 1.37 | 2.75 |
| 34 | (CH₃)Si(OCH₃)₃ | 12.2 | 0.085 | 100 | 1.37 | 2.75 |
| 35 | (CH₃)Si(OCH₂CH₃)₃ | 17.0 | 0.086 | 100 | 1.37 | 2.75 |

Example 5—Preparation of Silicon Tetrachloride from Various Ratios of Tetramethoxysilane, Excess Thionyl Chloride, and Dimethylformamide In Run No.'s 36-39, a warmed (55° C.) mixture of tetramethoxysilane, thionyl chloride, and dimethylformamide (DMF) is refluxed for a predetermined amount of time. The reflux time, the ratio of thionyl chloride to silane, and the ratio of DMF to silane in each run are provided in Table 4 along with the percent yield of silicon tetrachloride. The amount of each component used in each run is provided in Table 13. The reaction mixture in each run is fractionally distilled using a 29 cm column with glass helices packing at atmospheric pressure with the fraction distillate in the temperature range of 53-62° C. being collected. The composition and percent yield was determined using the distillate and $^{29}$Si NMR.

TABLE 13

| Run No. | Tetramethoxysilane | | Thionyl Chloride | | DMF |
|---|---|---|---|---|---|
| | volume (mL) | mmol | volume (mL) | mmol | mL |
| 36 | 12.7 | 0.086 | 100 | 1.37 | 2.75 |
| 37 | 25.5 | 0.171 | 100 | 1.37 | 2.75 |
| 38 | 12.7 | 0.086 | 100 | 1.37 | 2.75 |
| 39 | 12.7 | 0.086 | 100 | 1.37 | 1.38 |

Example 6—Preparation of Silicon Tetrachloride from Tetramethoxysilane, Excess Thionyl Chloride, and Dimethylformamide at Various Temperatures In Run No.'s 40-47, a mixture of tetramethoxysilane, thionyl chloride, and dimethylformamide (DMF) is warmed at a predetermined temperature. More specifically, Run No.'s 40 and 45 is warmed at 55° C., Run No. 41 is warmed at 45° C., Run No.'s 42-43 is warmed at 35° C., Run No. 46 is warmed at 38° C., and Run No.'s 44 and 47 are warmed at 20-25° C. Then each mixture in Run No.'s 40-47 is refluxed for a predetermined amount of time. The reflux time, the ratio of thionyl chloride to silane, and the ratio of DMF to silane in each run are provided in Table 4 along with the percent yield of silicon tetrachloride. The amount of each component used in each run is provided in Table 14. The reaction mixture in each run is fractionally distilled using a 29 cm column with glass helices packing at atmospheric pressure. The fraction distilling in the temperature range of 53-62° C. is collected and the composition and percent yield determined using the distillate and $^{29}$Si NMR.

TABLE 14

| Run No. | Tetramethoxysilane | | Thionyl Chloride | | DMF |
|---|---|---|---|---|---|
| | volume (mL) | mmol | volume (mL) | mmol | mL |
| 40 | 12.7 | 0.086 | 100 | 1.37 | 2.75 |
| 41 | 25.5 | 0.086 | 100 | 1.37 | 2.75 |
| 42 | 12.7 | 0.086 | 100 | 1.37 | 2.75 |
| 43 | 12.7 | 0.086 | 100 | 1.37 | 2.75 |
| 44 | 12.7 | 0.086 | 100 | 1.37 | 2.75 |
| 45 | 25.5 | 0.171 | 100 | 1.37 | 1.38 |
| 46 | 25.5 | 0.171 | 100 | 1.37 | 1.38 |
| 47 | 25.5 | 0.171 | 100 | 1.37 | 1.38 |

Example 7—Preparation of Silicon Tetrachloride from Tetramethoxysilane and Excess Thionyl Chloride in the Presence of Various Catalysts In Run No.'s 36, and 48-52, a warmed (55° C.) mixture of tetramethoxysilane, thionyl chloride, and a catalyst is refluxed for a predetermined amount of time. The reflux time, the composition of the catalyst, the ratio of thionyl chloride to silane, and the ratio of catalyst to silane in each run are provided in Table 5 along with the percent yield of silicon tetrachloride. The amount of each component used in each run is provided in Table 15. The reaction mixture in each run is fractionally distilled using a 29 cm column with glass helices packing at atmospheric pressure. The fraction distilling in the temperature range of 53-62° C. is collected and the composition and percent yield determined for the distillate using $^{29}$Si NMR.

TABLE 15

| Run No. | Tetramethoxysilane | | Thionyl Chloride | | Catalyst | |
|---|---|---|---|---|---|---|
| | volume (mL) | mmol | volume (mL) | mmol | mL | grams |
| 36 | 12.7 | 0.086 | 100 | 1.37 | 2.75 | — |
| 48 | 12.7 | 0.086 | 100 | 1.37 | 1.65 | — |
| 49 | 12.7 | 0.086 | 100 | 1.37 | 2.5 | — |
| 50 | 12.7 | 0.086 | 100 | 1.37 | 5.0 | — |
| 51 | 12.7 | 0.086 | 100 | 1.37 | — | 2.28 |
| 52 | 12.7 | 0.086 | 100 | 1.37 | — | 4.56 |

Example 8—Preparation of Silicon Tetrachloride from Higher Tetraalkoxysilanes and Excess Thionyl Chloride in Presence of Dimethylformamide Catalyst In Run No.'s 53-56, a warmed (55° C.) mixture of a tetralkoxysilane, thionyl chloride, and dimethylformamide (DMF) is refluxed for a predetermined amount of time. The reflux time, the composition of the tetraalkoxysilane, the ratio of thionyl chloride to silane, and the ratio of DMF to silane in each run are provided in Table 6 along with the percent yield of silicon tetrachloride. The amount of each component used in each run is provided in Table 16. The reaction mixture in each run is fractionally distilled using a 29 cm column with glass helices packing at atmospheric pressure. The fraction distilling in the temperature range of 53-62° C. is collected and the composition and percent yield determined for the distillate using $^{29}$Si NMR.

TABLE 16

| Run No. | Tetraalkoxysilane | | | Thionyl Chloride | | DMF |
|---|---|---|---|---|---|---|
| | Composition | volume (mL) | mmol | volume (mL) | mmol | volume (mL) |
| 53 | Si(OCH$_3$)$_4$ | 12.7 | 0.086 | 100 | 1.37 | 2.75 |
| 54 | Si(OCH$_2$CH$_3$)$_4$ | 19.1 | 0.086 | 100 | 1.37 | 2.75 |
| 55 | Si(OCH$_2$CH$_2$CH$_3$)$_4$ | 24.7 | 0.086 | 100 | 1.37 | 2.75 |
| 56 | Si(OCH$_2$CH$_2$CH$_2$CH$_3$)$_4$ | 30.5 | 0.086 | 100 | 1.37 | 2.75 |

Example 9—Preparation of Chloro-Substituted Silanes from Alkoxysilanes and Excess Hydrogen Chloride In Run No.'s 57-60, an alkoxysilane is treated with hydrogen chloride at a predetermined temperature for a predetermined amount of time. The predetermined temperature and time, the composition of the alkoxysilane, and the ratio of hydrogen chloride to silane in each run are provided in Table 7 along with the composition of the chloro-substituted silane and its relative intensity obtained via $^{29}$Si NMR. The amount of each component used in each run is provided in Tables 17(a-c).

TABLE 17a

| Run | Alkylalkoxysilane | | Aqueous HCl | |
|---|---|---|---|---|
| No. | volume (mL) | mol | volume (mL) | mol |
| 57 | 6.9 | 0.05 | 39 | 0.47 |

TABLE 17b

| Run | Alkylalkoxysilane | | Hydrogen Chloride | |
|---|---|---|---|---|
| No. | volume (mL) | mol | volume (mL/min) | mol |
| 58 | 2.5 | 0.017 | 78 | 0.21 |
| 59 | 2.5 | — | 78 | — |

TABLE 17c

| Run | Alkylalkoxysilane | | Hydrogen Chloride | |
|---|---|---|---|---|
| No. | volume (mL) | mol | volume (mL/min) | mol |
| 60 | 2.5 | 0.017 | 78 | 0.07 |

In Run No. 57, the reaction mixture also included 10 mL (0.076 mol) hexanes in which the organic or hexane layer was sampled to ascertain the composition and yield of the chloro-substituted silane product. In Run No. 60, the liquid HCl was formed by passing hydrogen chloride gas at a rate of about 78 mL/minute into a liquid nitrogen cooled trap for 20 minutes.

Example 10—Preparation of Silicon Tetrachloride from Tetraacetoxysilane and an Excess of Thionyl Chloride in the Presence of a Catalyst In Run No.'s 61-63, a hot (120° C.) mixture of tetraacetoxysilane, thionyl chloride, and a catalyst is mixed for a predetermined amount of time. The mixing time, the composition of the catalyst, the ratio of thionyl chloride to silane, and the ratio of catalyst to silane in each run are provided in Table 8 along with the percent yield of silicon tetrachloride. The amount of each component used in each run is provided in Table 18. The reaction mixture in each run is sampled and the composition, as well as the percent yield determined using $^{29}$Si NMR.

TABLE 18

| Run No. | Tetraacetoxysilane grams | Catalyst DMF (μL) | SOCl$_2$ volume (mL) |
|---|---|---|---|
| 61 | 0.11 | 10 | 1.5 |
| 62 | 0.13 | 10 | 1.8 |
| 63 | 0.13 | 10 | 1.8 |

Example 11—Determining Relative Intensity of Chloro-Substituted Silanes

The various chloro-substituted silane products collected from the different experimental runs are identified and their relative intensities measured using $^{29}$Si nuclear magnetic resonance (NMR) spectroscopy, More specifically, a 600 MHz Varian Inova NMR spectrometer is used for each measurement generally with a total of 128 scans being taken for each of the different experimental runs and processing done with a line broadening of 10. The instrument settings generally used in the collection of data include a temperature of 25° C., a spinning rate of 25 Hz, a pulse width of 5 μs, a spectrum width of 60 kHz, a recycle delay of 3 seconds, and a gated decoupled acquisition time of 1.0 second. The relative intensity of each chloro-substituted silane is determined on a scale of 1-10 with 10 being the most intense.

Figure 4:
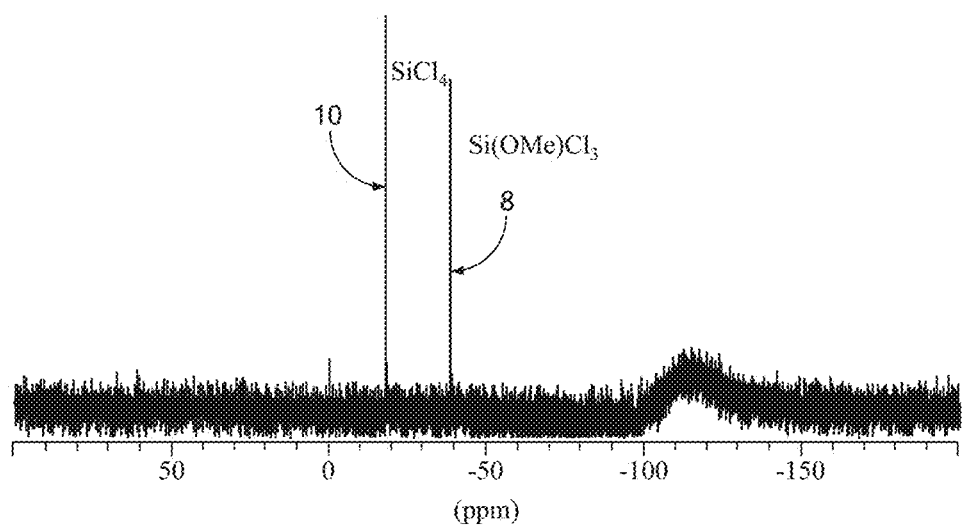
FIG. 4 is a $^{29}$Si nuclear magnetic resonance spectrum of the chloro-substituted silanes prepared according to the teachings of the present disclosure in Run No. 3.

A specific example of the $^{29}$Si NMR spectrum obtained for Run No. 3 is provided in FIG. 4. In this spectrum the identified chloro-substituted silanes are silicon tetrachloride and trichloromethoxysilane with relative intensities of 10 and 8, respectively (see FIG. 4 and Table 1).

One skilled in the art will understand that the properties and reaction conditions measured for the reactions described in Run No.'s 1-64 as described in Tables 1-8 represent properties and conditions that are routinely measured and can be obtained by multiple different methods. The methods described herein represent one such method and other methods may be utilized without exceeding the scope of the present disclosure.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of preparing chloro-substituted silanes, the method comprising the steps of:
    providing an alkoxysilane having the formula $(R'O)_{4-x}SiR_x$, where R and R' are independently selected alkyl groups comprising one or more carbon atoms and x is 0, 1, 2, or 3;
    providing a chlorinating agent;
    providing a catalyst;
    allowing the alkoxysilane to react with the chlorinating agent in the presence of the catalyst to form the chloro-substituted silanes along with multiple by-products; the chloro-substituted silanes having the formula $(R'O)_{4-x-y}SiR_xCl_y$; where x is 0, 1, 2, or 3; y is 1, 2, 3, or 4; and one of the by-products is an alkyl chloride; and
    separating the chloro-substituted silanes from the by-products.

2. The method of claim 1, wherein the chlorinating agent is one selected from the group of i) thionyl chloride, ii) sulfuryl chloride, iii) phosphorus oxychloride, iv) phosphorus trichloride, v) phosphorus pentachloride, and mixtures of two or more of groups i)-v).

3. The method of claim 1, wherein the catalyst is one selected from the group of i) dimethylformamide, ii) dimethylacetamide, iii) pyridine, iv) triethylamine, (chloromethylene)dimethyliminium chloride, and mixtures of two or more of groups i)-iv).

4. The method of claim 1, wherein the alkyl groups, R and R', are selected to be i) a methyl group, ii) an ethyl group, iii) a propyl group, iv) a butyl group, v) a phenyl group or a mixture of two or more of groups i)-v).

5. The method of claim 1, wherein the method further comprises the step of separating the alkyl chloride from the by-products.

6. The method of claim 1, wherein the chlorinating agent is provided in an amount that is greater than the stoichiometric amount necessary to completely react with the amount of alkoxysilane provided.

7. The method of claim 1, wherein the reaction between the alkoxysilane and the chlorinating agent is performed using at least one selected from the group of i) temperatures from 5° C. to 300° C., ii) a predetermined time up to 168 hours, and iii) a pressure that is equal to or greater than atmospheric pressure and less than or equal to 34 atmospheres (500 psi).

8. The method of claim 2, wherein the chlorinating agent is thionyl chloride.

9. The method of claim 1, wherein the chloro-substituted silanes include at least 50 wt. % or more silicon tetrachloride.

* * * * *